(12) United States Patent
Herrera et al.

(10) Patent No.: US 11,813,419 B2
(45) Date of Patent: *Nov. 14, 2023

(54) DOUBLE BALLOON CATHETER HAVING A LOBED INNER BALLOON

(71) Applicant: BIOSENSE WEBSTER (ISRAEL) LTD., Yokneam (IL)

(72) Inventors: Kevin Justin Herrera, West Covina, CA (US); Assaf Govari, Haifa (IL); Andres Claudio Altmann, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 285 days.

This patent is subject to a terminal disclaimer.

(21) Appl. No.: 17/083,260

(22) Filed: Oct. 28, 2020

(65) Prior Publication Data

US 2021/0060313 A1    Mar. 4, 2021

Related U.S. Application Data

(63) Continuation of application No. 15/360,967, filed on Nov. 23, 2016, now Pat. No. 10,821,272.

(51) Int. Cl.
*A61B 18/14* (2006.01)
*A61B 5/00* (2006.01)
(Continued)

(52) U.S. Cl.
CPC ......... *A61M 25/1011* (2013.01); *A61B 6/481* (2013.01); *A61B 6/485* (2013.01);
(Continued)

(58) Field of Classification Search
CPC ..... A61B 18/14; A61B 18/1492; A61B 18/02; A61B 18/00
See application file for complete search history.

(56) References Cited

U.S. PATENT DOCUMENTS

| 5,391,199 A | 2/1995 | Ben-Haim |
| 5,443,489 A | 8/1995 | Ben-Haim |

(Continued)

FOREIGN PATENT DOCUMENTS

| CN | 102271750 A | 12/2011 |
| CN | 104644161 A | 5/2015 |

(Continued)

OTHER PUBLICATIONS

Extended European Search Report for European Application No. EP17203142, dated Apr. 4, 2018, 10 pages.

*Primary Examiner* — Jon Eric C Morales
(74) *Attorney, Agent, or Firm* — Calderon Safran & Cole P.C.; Etan S. Chatlynne

(57) ABSTRACT

An apparatus, including a flexible insertion tube having a distal end for insertion into a body cavity, and first and second conduits configured to deliver first and second fluids, respectively, to the distal end. The distal end includes a first balloon coupled to the first conduit so that the first fluid inflates the first balloon and is delivered, via one or more spray ports in the first balloon, to tissue in the body cavity, a second balloon contained within the first balloon and coupled to the second conduit so that the second fluid inflates the second balloon, and multiple splines including a flexible, resilient material and extending along a longitudinal axis of the distal end, and configured to constrain the second balloon so that inflation of the second balloon creates lobes that form, along the longitudinal axis between the lobes, channels that direct the first fluid to the spray ports.

13 Claims, 5 Drawing Sheets

(51) Int. Cl.
  *A61M 25/10* (2013.01)
  *A61B 6/00* (2006.01)
  *A61B 17/22* (2006.01)
  *A61B 90/00* (2016.01)
  *A61B 17/00* (2006.01)
  *A61B 18/00* (2006.01)

(52) U.S. Cl.
  CPC .............. *A61B 18/1492* (2013.01); *A61B 2017/00991* (2013.01); *A61B 2017/22054* (2013.01); *A61B 2018/00029* (2013.01); *A61B 2018/00255* (2013.01); *A61B 2018/00357* (2013.01); *A61B 2018/00577* (2013.01); *A61B 2090/3933* (2016.02); *A61B 2090/3966* (2016.02); *A61M 2025/105* (2013.01); *A61M 2025/1013* (2013.01); *A61M 2025/1061* (2013.01); *A61M 2205/50* (2013.01); *A61M 2205/502* (2013.01); *A61M 2205/52* (2013.01)

(56) References Cited

U.S. PATENT DOCUMENTS

| | | |
|---|---|---|
| 5,558,091 A | 9/1996 | Acker et al. |
| 5,814,016 A | 9/1998 | Valley et al. |
| 5,944,022 A | 8/1999 | Nardella et al. |
| 5,983,126 A | 11/1999 | Wittkampf |
| 6,172,499 B1 | 1/2001 | Ashe |
| 6,177,792 B1 | 1/2001 | Govari et al. |
| 6,456,864 B1 | 9/2002 | Swanson et al. |
| 6,491,711 B1 | 12/2002 | Durcan |
| 6,690,963 B2 | 2/2004 | Ben-Haim et al. |
| 6,788,967 B2 | 9/2004 | Ben-Haim et al. |
| 7,727,228 B2 | 6/2010 | Abboud et al. |
| 9,033,965 B2 | 5/2015 | Ingle et al. |
| 9,907,610 B2 | 3/2018 | Beeckler et al. |
| 10,821,272 B2 * | 11/2020 | Herrera .............. A61B 18/1492 |
| 2014/0018794 A1 | 1/2014 | Anderson et al. |
| 2014/0358137 A1 | 12/2014 | Hu |
| 2016/0317221 A1 | 11/2016 | Rioux |
| 2018/0140807 A1 | 5/2018 | Herrera et al. |
| 2019/0298441 A1 | 10/2019 | Clark et al. |

FOREIGN PATENT DOCUMENTS

| | | |
|---|---|---|
| EP | 2528526 A1 | 12/2012 |
| EP | 2076308 B1 | 2/2013 |
| EP | 2875790 A2 | 5/2015 |
| EP | 3326563 A1 | 5/2018 |
| JP | 2002535033 A | 10/2002 |
| JP | 2012502759 A | 2/2012 |
| JP | 2013521937 A | 6/2013 |
| JP | 2015100706 A | 6/2015 |
| JP | 2016116863 A | 6/2016 |
| WO | 2016176567 A1 | 11/2016 |

* cited by examiner

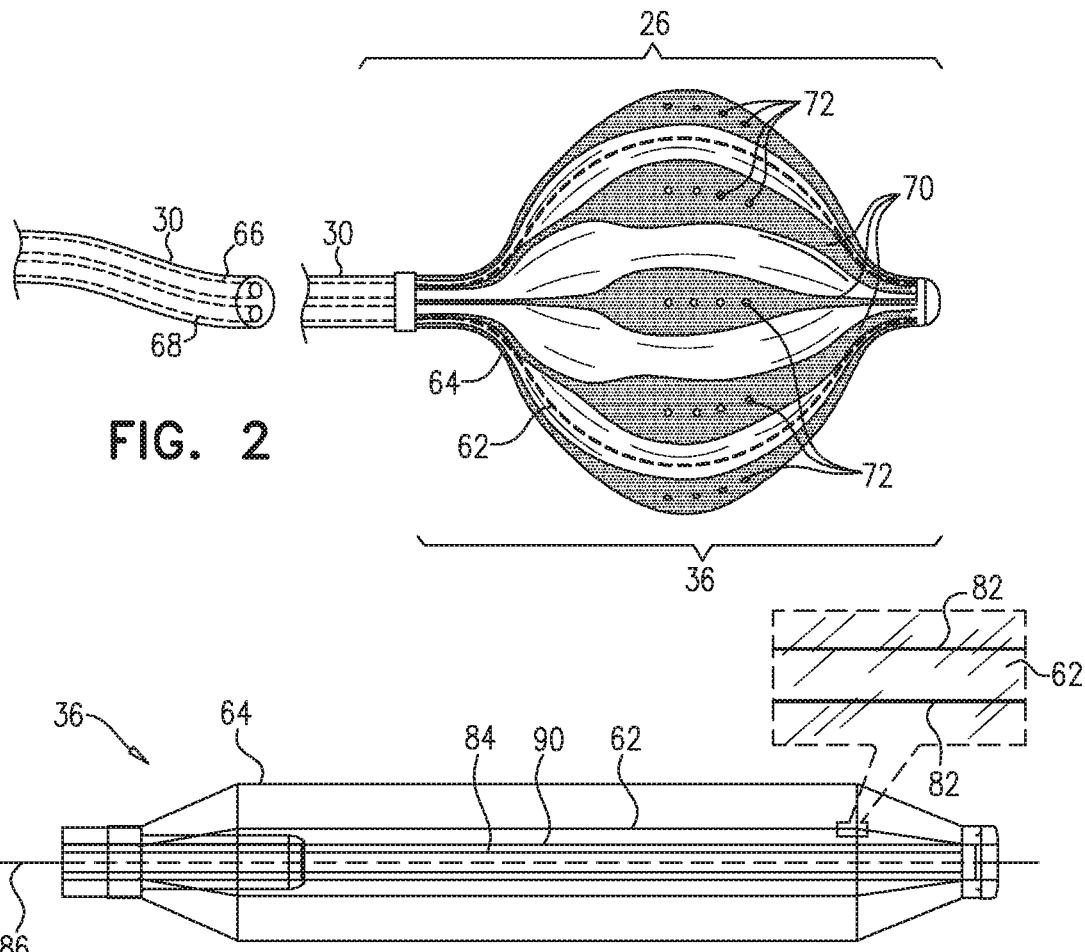
FIG. 2
FIG. 3
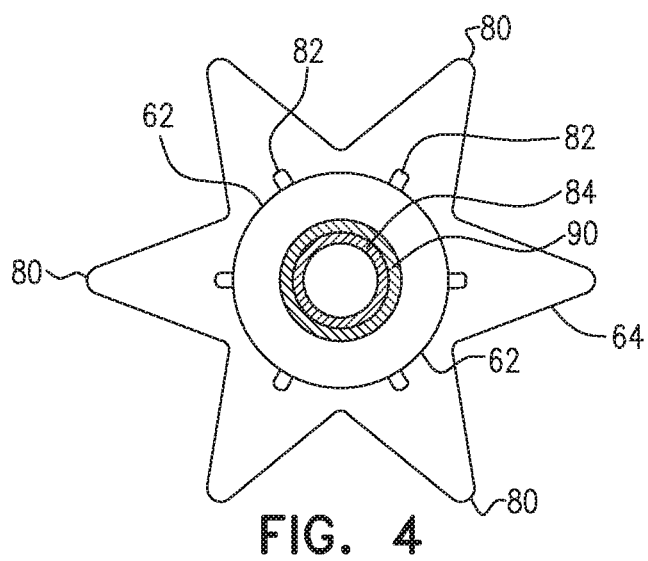
FIG. 4

DOUBLE BALLOON CATHETER HAVING A LOBED INNER BALLOON

CROSS-REFERENCE TO CO-PENDING APPLICATION

The present application is a Continuation Applications under 35 U.S.C. § 120 of U.S. patent application Ser. No. 15/360,967, filed Nov. 23, 2016. The entire contents of this application is incorporated by reference herein in its entirety.

FIELD OF THE INVENTION

The present invention relates generally to invasive probes, and specifically to an invasive probe configured to irrigate tissue during a medical procedure.

BACKGROUND OF THE INVENTION

A wide range of medical procedures involve placing objects such as sensors, tubes, catheters, dispensing devices, and implants, within the body. An example of a medical procedure that is performed with a catheter is ablation of body tissue such as heart tissue. The ablation may be used to cure a variety of cardiac arrhythmia, as well as to manage atrial fibrillation. Such procedures are known in the art. Other medical procedures using ablation of body tissue, such as treating varicose veins, are also known in the art. The ablation energy for these procedures may be in the form of radio-frequency (RF) energy, which is supplied to the tissue via one or more electrodes of a catheter used for the procedures.

The description above is presented as a general overview of related art in this field and should not be construed as an admission that any of the information it contains constitutes prior art against the present patent application.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

There is provided, in accordance with an embodiment of the present invention, a medical apparatus, including a flexible insertion tube having a distal end for insertion into a body cavity, first and second conduits contained within the flexible insertion tube and configured to deliver first and second fluids, respectively, to the distal end, and a terminal member fixed to the distal end of the insertion tube and including a first balloon including one or more spray ports and coupled to the first conduit so that the first fluid inflates the first balloon and is delivered, via the one or more spray ports, to tissue in the body cavity, a second balloon contained within the first balloon and coupled to the second conduit so that the second fluid inflates the second balloon, and multiple splines including a flexible, resilient material and extending along a longitudinal axis of the terminal member, and configured to constrain the second balloon so that inflation of the second balloon creates lobes that form, along the longitudinal axis between the lobes, channels that direct the first fluid from the first conduit to the one or more spray ports.

In some embodiments, the first fluid includes an irrigation fluid, and the second fluid includes a contrast agent that can provide radiopacity for a fluoroscopy unit. In additional embodiments, the medical apparatus according may include one or more electrodes mounted on the first balloon and configured to convey radio-frequency energy to tissue in a body cavity.

In further embodiments the medical apparatus may include a telescoping shaft contained within the second balloon and configured to retract upon inflating the second balloon and to extend upon deflating the second balloon. In embodiments including the telescoping shaft, the medical apparatus may include a flexible sleeve surrounding the telescoping shaft and configured to prevent the second fluid from entering the insertion tube.

In some embodiments, the splines may have cross-sections selected from a group consisting of rectangular and elliptical cross-sections. In additional embodiments, the splines can be embedded in the second balloon. In further embodiments, the splines can be affixed to an outer surface of the second balloon. In supplemental embodiments, the splines can be positioned within the second balloon.

There is also provided, in accordance with an embodiment of the present invention, a method, including inserting a distal end of flexible insertion tube into a body cavity, the flexible insertion tube containing first and second conduits configured to deliver first and second fluids, respectively, to a terminal member fixed to the distal end of the insertion tube, the terminal member including a first balloon including one or more spray ports and coupled to the first conduit, a second balloon contained within the first balloon and coupled to the second conduit, and multiple splines including a flexible, resilient material and extending along a longitudinal axis of the terminal member and configured to constrain the second balloon. The method also includes conveying, via the first conduit, the first fluid in order to inflate the first balloon and to deliver, via the one or more spray ports, the first fluid to tissue in the body cavity, and conveying, via the second conduit, the second fluid in order to inflate the second balloon and to create, using the splines, lobes on the second balloon that form, along the longitudinal axis between the lobes, channels that direct the first fluid from the first conduit to the one or more spray ports.

There is additionally provided, in accordance with an embodiment of the present invention, a method, including providing a medical probe for insertion into a body cavity, the medical probe including, at its distal end, an outer balloon including one or more spray ports and an inner balloon contained within the outer balloon, injecting a contrast agent into the inner balloon so as to inflate the inner balloon, visualizing the distal end of the medical probe in the body cavity by imaging the contrast agent in the inner balloon, thereby enabling the distal end to be maneuvered to a target location, and conveying, via the one or more spray ports in the outer balloon, irrigation fluid to tissue at the target location.

In some embodiments, the contrast agent provides radiopacity for a fluoroscopy unit, and visualizing the distal end may include capturing, by the fluoroscopy unit, an image of the contrast agent in the inner balloon, and presenting the image on a display.

There is further provided, in accordance with an embodiment of the present invention, an apparatus, including a medical probe configured for insertion into a body cavity and including, at its distal end, an outer balloon including one or more spray ports and an inner balloon contained within the outer balloon, and a control console configured to inject a contrast agent into the inner balloon so as to inflate the inner balloon, to visualize the distal end of the medical probe in the body cavity by imaging the contrast agent in the inner balloon, thereby enabling the distal end to be maneuvered to a target location, and to convey, via the one or more spray ports in the outer balloon, irrigation fluid to tissue at the target location.

There is also provided, in accordance with an embodiment of the present invention, a computer software product, operated in conjunction with a medical probe for insertion into a body cavity, the medical probe including, at its distal end, an outer balloon including one or more spray ports and an inner balloon contained within the outer balloon, the product including a non-transitory computer-readable medium, in which program instructions are stored, which instructions, when read by a computer, cause the computer, upon injecting a contrast agent into the inner balloon in order to inflate the inner balloon, to visualize the distal end of the medical probe in the body cavity by imaging the contrast agent in the inner balloon, thereby enabling the distal end to be maneuvered to a target location while conveying, via the one or more spray ports in the outer balloon, irrigation fluid to tissue at the target location.

BRIEF DESCRIPTION OF THE DRAWINGS

The disclosure is herein described, by way of example only, with reference to the accompanying drawings, in which:

FIG. 2 is a schematic pictorial illustration of a distal end of the double balloon catheter, in accordance with an embodiment of the present invention;

FIG. 3 is a schematic cross-sectional longitudinal view of the distal end with the inner balloon in an extended state, in accordance with an embodiment of the present invention;

FIG. 4 is a schematic cross-sectional latitudinal view of the distal end with the inner and the outer balloons in extended states, in accordance with an embodiment of the present invention;

DETAILED DESCRIPTION OF EMBODIMENTS

Overview

Figure 1:
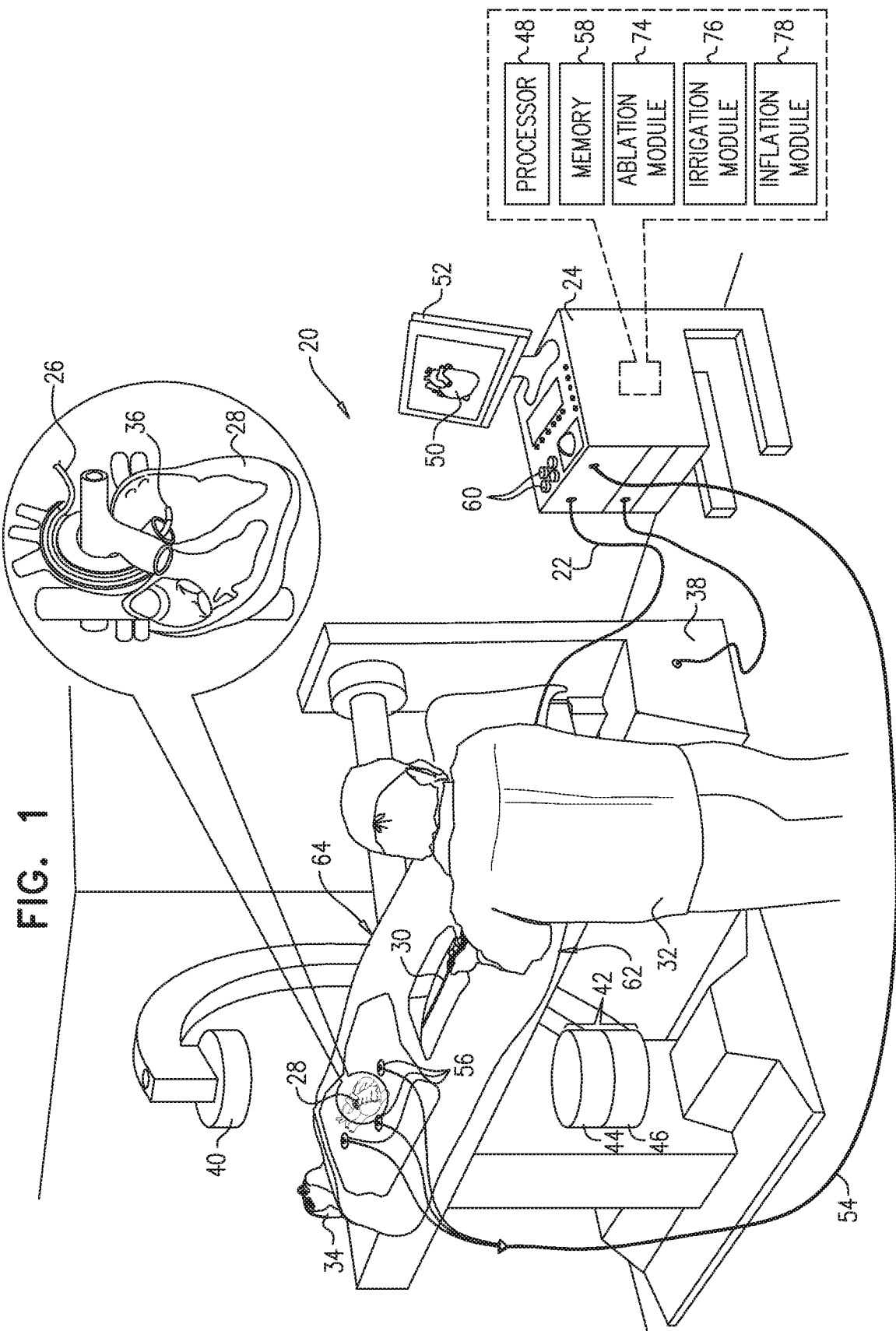
FIG. 1 is a schematic pictorial illustration of a medical system configured to perform an ablation procedure using a double balloon catheter comprising an inner balloon surrounded by an outer balloon, in accordance with an embodiment of the present invention.

Various therapeutic procedures such as cardiac ablation use an invasive medical probe such as a catheter that is inserted into a patient's body. During an ablation procedure on a heart, there may be local overheating of the heart surface being ablated, as well as of the heart tissue underlying the surface. The surface overheating may be manifested as charring, and the overheating of the underlying tissue may cause other damage to the tissue, even leading to penetration of the tissue. To control the temperature of the surface and the underlying tissue, the region being ablated may be irrigated with an irrigation fluid, typically saline, in order to prevent charring.

In embodiments of the present invention, a medical probe such as a catheter comprises a flexible insertion tube having a distal end for insertion into a body cavity, and first and second conduits contained within the flexible insertion tube and configured to deliver first and second fluids, respectively, to the distal end. The medical probe also comprises a terminal member that is fixed to the distal end and comprises a first balloon (also referred to herein as an outer balloon), a second balloon (also referred to herein as an inner balloon) contained within the first balloon, and multiple splines that extend along a longitudinal axis of the terminal member. The first balloon comprises one or more irrigation spray ports and is coupled to the first conduit so that the first fluid inflates the first balloon, and is delivered, via the one or more spray ports, to tissue in the body cavity. The second balloon is coupled to the second conduit so that the second fluid received from the second conduit inflates the second balloon. The multiple splines comprise a shape-memory alloy and extend along a longitudinal axis of the terminal member, so that upon inflating the second balloon, the splines constrain the inflation of the second balloon in order to create lobes that form, along the longitudinal axis between the lobes, channels that direct the first fluid from the first conduit to the one or more spray ports.

In some embodiments, the first fluid may comprise an irrigation fluid. While supplying the outer balloon with the irrigation fluid (i.e., to be conveyed to tissue in a body cavity) during an ablation procedure, the inner balloon can control the overall volume (i.e., of both balloons). Additionally, as described hereinbelow, the inner balloon can be independently inflated or deflated, thereby significantly shortening the inflation/deflation time of the outer balloon, and reducing the stress on the outer balloon.

In additional embodiments, upon injecting a fluoroscopic contrast agent into the inner balloon while inflating the inner balloon, the distal end of the medical probe can be visualized fluoroscopically in the body cavity by imaging the contrast medium in the inner balloon, thereby enabling the distal end to be maneuvered to a target location. The visualization of the distal end can be used by an operator while the medical probe conveys, via the one or more spray ports in the outer balloon, irrigation fluid to tissue at the target location.

System Description

FIG. 1 is a schematic pictorial illustration of a medical system 20 comprising a medical probe 22 (e.g., a catheter) and a control console 24, and FIG. 2 is a schematic illustration of a distal end 26 of the medical probe used in the medical system, in accordance with an embodiment of the present invention. System 20 may be based, for example, on the CARTO® system, produced by Biosense Webster Inc. (Diamond Bar, Calif., U.S.A.). In embodiments described hereinbelow, it is assumed that probe 22 is used for diagnostic or therapeutic treatment, such as performing ablation of heart tissue in a heart 28. Alternatively, probe 22 may be used, mutatis mutandis, for other therapeutic and/or diagnostic purposes in the heart or in other body organs.

Probe 22 comprises an insertion tube 30, which an operator 32 inserts into a lumen, such as a chamber of heart 28, of a patient 34. In the example shown in FIG. 1, operator 32 inserts insertion tube 30 through the vascular system of patient 34 so that a terminal member 36 fixed to distal end 26 enters a chamber of heart 28. Operator 32 can use a fluoroscopy unit 38 to visualize distal end 26 inside heart 28. Fluoroscopy unit 38 comprises an X-ray source 40, positioned above patient 34, which transmits X-rays through the patient. A flat panel detector 42, positioned below patient 34, comprises a scintillator layer 44 which converts the X-rays which pass through patient 34 into light, and a sensor layer 46 which converts the light into electrical signals. Sensor layer 46 typically comprises a two dimensional array of photodiodes, where each photodiode generates an electrical signal in proportion to the light detected by the photodiode.

Control console 24 comprises a processor 48 that converts electrical signals from fluoroscopy unit 38 into an image 50, which the processor presents as information regarding the procedure on a display 52. Display 52 is assumed, by way of example, to comprise a cathode ray tube (CRT) display or a flat panel display such as a liquid crystal display (LCD), light emitting diode (LED) display or a plasma display. However other display devices can also be employed to implement embodiments of the present invention. In some embodiments, display 52 may comprise a touchscreen configured to accept inputs from operator 32, in addition to presenting image 50.

In the example of FIG. 1, console 24 is connected, via a cable 54, to body surface electrodes, which typically comprise adhesive skin patches 56 that are affixed to patient 34. Processor 48 determines position coordinates of distal end 26 inside heart 28 based on impedances measured between patches 56 and one or more electrodes 70 (FIG. 2) mounted on distal end 26. Although the medical system shown in FIG. 1 uses impedance-based sensing to measure a location of distal end 26, other position tracking techniques may be used (e.g., magnetic-based sensors). Impedance-based position tracking techniques are described, for example, in U.S. Pat. Nos. 5,983,126, 6,456,864 and 5,944,022, whose disclosures are incorporated herein by reference. Magnetic position tracking techniques are described, for example, in U.S. Pat. Nos. 5,391,199, 5,443,489, 6,788,967, 6,690,963, 5,558, 091, 6,172,499 6,177,792, whose disclosures are incorporated herein by reference. The method of position sensing described hereinabove is implemented in the above-mentioned CARTO™ system and is described in detail in the patents cited above.

Processor 48 typically comprises a general-purpose computer, with suitable front end and interface circuits for receiving signals from probe 22 and controlling the other components of console 24. Processor 48 may be programmed in software to carry out the functions that are described herein. The software may be downloaded to console 24 in electronic form, over a network, for example, or it may be provided on non-transitory tangible media, such as optical, magnetic or electronic memory media. Alternatively, some or all of the functions of processor 48 may be carried out by dedicated or programmable digital hardware components.

Based on the signals received from probe 22 and other components of system 20, processor 48 drives display 52 to update image 50 to present a current position of distal end 26 in the patient's body, as well as status information and guidance regarding the procedure that is in progress. Processor 48 stores data representing image 50 in a memory 58. In some embodiments, operator 32 can manipulate image 50 using one or more input devices 60. In embodiments, where display 52 comprises a touchscreen display, operator 32 can manipulate image 50 via the touchscreen display.

As shown in FIG. 2, terminal member 36 comprises an inner balloon 62 that is contained within an outer balloon 64, and insertion tube 30 comprises an irrigation conduit 66 and an inflation conduit 68 that are contained within the insertion tube. Irrigation conduit 66 is coupled to outer balloon 64, and enables irrigation fluid to be injected into the outer balloon. Inflation conduit 68 is coupled to inner balloon 62, and enables a fluid separate from the irrigation fluid to be injected into the inner balloon. In embodiments of the present invention, the fluid injected into the inner balloon may comprise a contrast-bearing fluid (also referred to herein as a contrast agent. Due to its configuration, medical probe 22 may also be referred to as a double balloon catheter.

In the example shown in FIG. 2, balloons 62 and 64 are inflated, and the outer balloon comprises electrodes 70 that typically comprise one or more thin metal layers formed over the outer balloon. Although not shown in FIG. 2 (and in FIGS. 3-6) for purposes of simplicity, terminal member 36 also comprises wires that convey radio-frequency energy from console 24 to electrodes 70, thermocouples that are configured to sense temperature, and position sensors that can aid navigation of distal end 26 in patient 34.

Outer balloon 64 comprises irrigation spray ports 72 that are configured to convey irrigation fluid from within the outer balloon to tissue in a body cavity such as heart 26 (e.g., during an ablation procedure). While the configuration in FIG. 2 shows irrigation spray ports 72 positioned within electrodes 72, positioning each of the irrigation points at any location on outer balloon 64 is considered to be within the spirit and scope of the present invention. The configuration of inner balloon 62 is described in the description referencing FIGS. 3 and 4 hereinbelow.

Control console 24 also comprises an ablation module 74, an irrigation module 76 and an internal balloon inflation module 78 (also referred to herein as inflation module 78). In operation, ablation module 74 monitors and controls ablation parameters such as the level and the duration of ablation power applied to ablation electrodes 70. Irrigation module 76 delivers, via irrigation conduit 66, an irrigation fluid to outer balloon 64, and monitors the flow of the irrigation fluid to the outer balloon. The outer balloon conveys irrigation fluid to body cavity tissue via irrigation spray ports 72. Inflation module 78 is configured to deliver, via inflation conduit 68, an inflation fluid to inner balloon 62 in order to inflate the inner balloon. Inflation module 78 is also configured to extract the inflation fluid from the inner balloon in order to deflate inner balloon 62.

The irrigation fluid is typically a saline solution that outer balloon delivers, via irrigation spray ports 72, to tissue in a body cavity during an ablation procedure in order to prevent charring. In some embodiments of the present invention, the inflation fluid comprises a contrast agent that can be used to enhance contrast of the inner balloon for medical imaging. For example, the contrast agent may be configured to provide radiopacity for fluoroscopy unit 38. The contrast agent enables console 24 to present to operator 32, on display 52, inner balloon 62, while outer balloon 64 is performing an ablation procedure and conveying, via the one or more irrigation spray ports, irrigation fluid to tissue in heart 28.

FIG. 3 is a schematic cross-sectional longitudinal view of terminal member 36 comprising inner balloon 62 and outer balloon 64 in extended (i.e., deflated) states, and FIG. 4 is a schematic cross-sectional latitudinal view of terminal member 36 with the inner and the outer balloons in extended states in accordance with an embodiment of the present invention. For purposes of visual simplicity, electrodes 70 and irrigation spray ports 72 are not shown in FIGS. 3 and 4. Inner balloon 62 typically comprises an elastic material such as silicone tubing or another polymer that is able to stretch while also having the ability to relax to its original (i.e., extended and non-inflated) tubular shape, and outer balloon 62 typically comprises materials such as Pellethane® produced by the Lubrizol Corporation (Wickliffe, Ohio, U.S.A.), polyurethane, Pebax® produced by Arkema S.A. (Colombes, France), nylon, polyethylene terephthalate (PET), or any blend or combination of these materials.

In embodiments of the present invention, the inflation of inner balloon 62 is constrained by a set of splines 82 that extend longitudinally about a telescoping shaft 84 that is enclosed within a thin flexible sleeve 90. Shaft 84 in turn extends along a longitudinal axis 86 of the terminal member. Telescoping shaft 84 typically comprises a concertina-like tube that enables the telescoping shaft to retract upon inflating the inner balloon and to extend upon deflating the inner balloon. In the example shown in FIG. 3, inner balloon 62 is deflated, and splines 82 return to their respective original states.

Splines 82 may have elliptical (e.g., circular) or rectangular (that may appear to be flat) cross-sections, and typically comprise a flexible, resilient material (e.g., a shape-memory alloy such nickel-titanium, also known as Nitinol). In some embodiments, splines 82 may be embedded within the elastic material of the inner balloon, and in alternative embodiments, the splines can be either affixed to the inner balloon's outer surface (i.e., in between the inner and the outer balloons, as shown in FIG. 4) or affixed to the inner balloon's inner surface (i.e., in between the inner balloon and sleeve 90). When inner balloon 62 is not inflated, splines 82 are configured to remain straight (i.e., respective "original states" for the splines), thus keeping the inner balloon extended, and upon inflating the inner balloon, the rectangular shape of the splines constrains them to bend in a single direction (i.e., outward from longitudinal axis 86). In addition to "straightening" terminal member 36 when inner balloon 62 is not inflated, the shape-memory alloy in splines 82 prevents the terminal member from "kinking" and therefore malfunctioning due to an error performed when manipulating insertion tube 30.

In operation, upon inflating balloons 62 and 64, telescoping shaft 84 is configured to retract, and splines 82 are configured to extend latitudinally in order to create lobes, as described hereinbelow in the description referencing FIG. 6. Likewise, upon deflating balloons 62 and 64, splines 82 return to their respective original (i.e., straightened) states, thereby extending telescoping shaft 84. While the example in FIG. 3 (and in FIG. 4, as described hereinbelow) shows inner balloon 62 in an extended state comprising lobes 88, configuring the inner balloon to have no lobes while the inner balloon is in an extended state is considered to be within the spirit and scope of the present invention. Inner balloon 62 is typically more compliant than outer balloon 64, thereby enabling the inner balloon to transition from a "tube" shape when not inflated to a spherical shape comprising the lobes described hereinbelow in the description referencing FIG. 6.

As described supra, telescoping shaft 84 is enclosed within a thin flexible sleeve 90. Sleeve 90 is typically made of silicone or a stretchable polymer that surrounds telescoping shaft 84 in order to act as a seal that prevents any back flow of inflation fluid from inner balloon 62 into the telescoping shaft and the bloodstream of the patient. Sleeve 90 stretches axially and relaxes as the nitinol wires shift the balloon from extended to inflated states.

Figure 5:
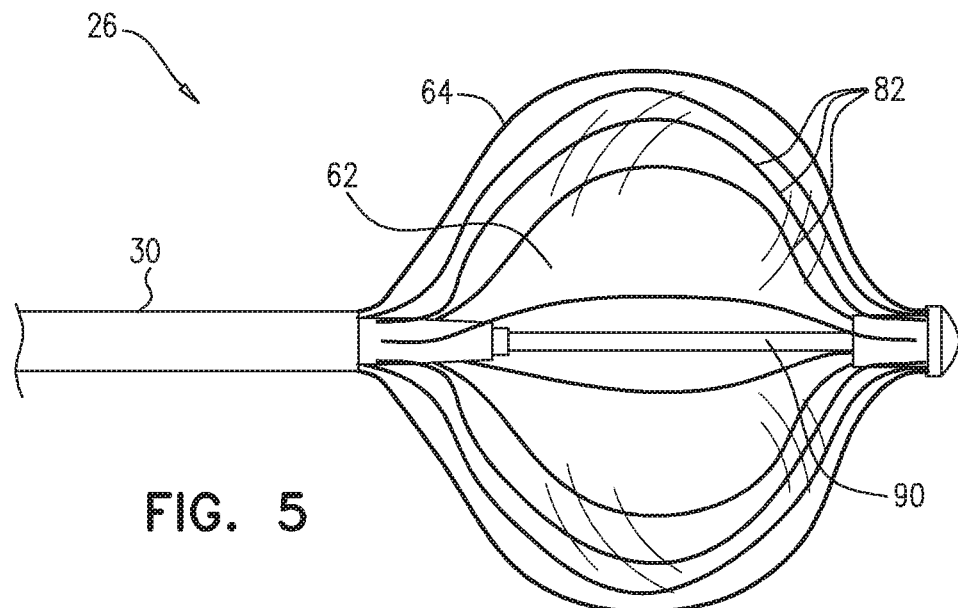
FIG. 5 is a schematic cross-sectional longitudinal view of the distal end with the inner and the outer balloons in inflated states, in accordance with an embodiment of the present invention.

As described supra, FIGS. 3 and 4 show terminal member 36 with inner balloon 64 in extended states. In the configuration shown in FIG. 4, inner balloon 62 has an elliptical latitudinal cross-section, and outer balloon 64 comprises lobes 80 that given the outer balloon a "star shaped" latitudinal cross-section. As shown in FIGS. 5 and 6 that are described hereinbelow, upon inflating the inner and the outer balloons, inner balloon 62 inflates to have a star shaped latitudinal cross-section, and outer balloon 64 inflates to have an elliptical latitudinal cross-section.

FIG. 5 is a schematic cross-sectional longitudinal view of terminal member 36 comprising balloons 62 and 64 in inflated states, in accordance with an embodiment of the present invention. In the example shown in FIG. 5, telescoping shaft 84 retracts longitudinally and splines 82 extend latitudinally upon inflating the balloons.

Figure 6:
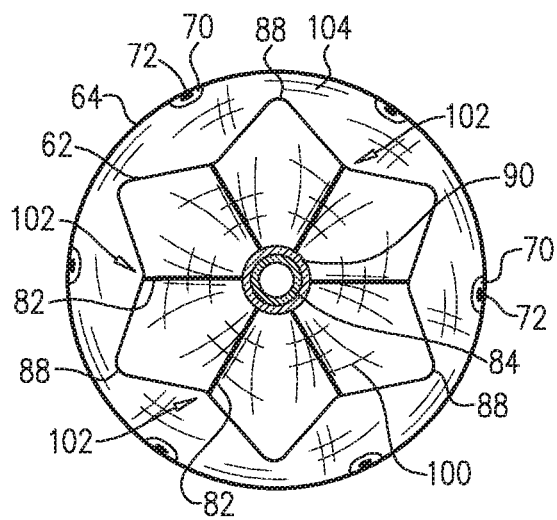
FIG. 6 is a schematic cross-sectional latitudinal view of the distal end with the inner and the outer balloons in inflated states, in accordance with an embodiment of the present invention.

FIG. 6 is a schematic cross-sectional latitudinal view of terminal member 36 comprising the inner and the outer balloons in inflated states, in accordance with an embodiment of the present invention. As inflation module 78 inflates inner balloon 62 by conveying an inflation fluid 100 to the inner balloon, splines 82 constrain the inflation of the inner balloon in order to create lobes 88 that form channels 102 (i.e., along longitudinal axis 86 between the lobes) that direct an irrigation fluid 104 from irrigation conduit 66 to irrigation spray ports 72.

Double Balloon Catheter Ablation and Irrigation

Figure 8:
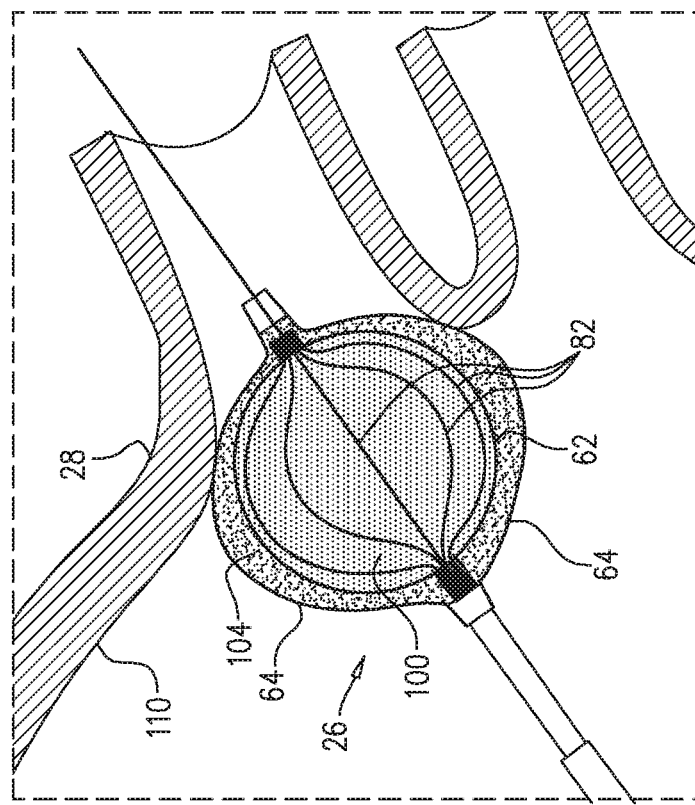
FIG. 8 is a schematic illustration showing a cut-away view of the distal end during the ablation procedure, in accordance with an embodiment of the present invention.
Figure 7:
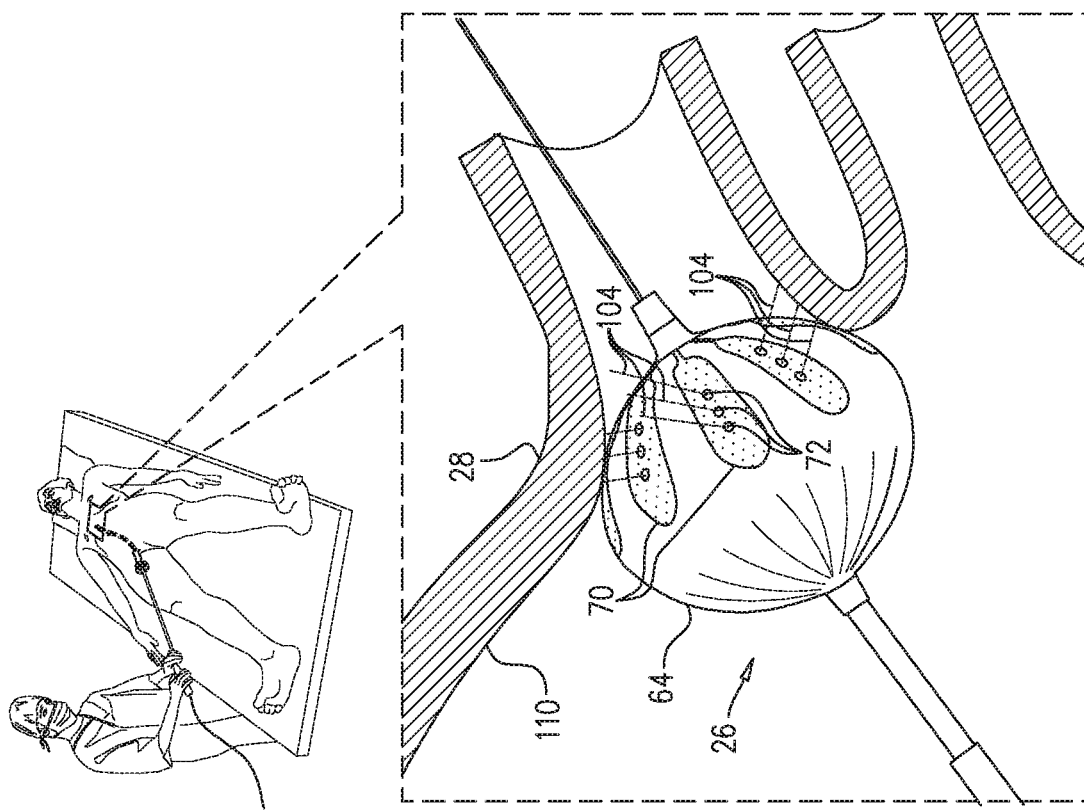
FIG. 7 is a schematic detail view showing the outer balloon in contact with endocardial tissue during an ablation procedure, in accordance with an embodiment of the present invention.

FIG. 7 is a schematic detail view showing outer balloon 64 in contact with endocardial tissue 110 of heart 28 during an ablation procedure, and FIG. 8 is a schematic illustration showing a cut-away view of terminal member 36 during the ablation procedure, in accordance with an embodiment of the present invention. As described supra, during some electrophysiological therapeutic procedures, such as cardiac ablation, it is typically important to regulate the temperature of the endocardial tissue. Therefore, during an ablation procedure performed using electrodes 70, as shown in FIG. 7, medical probe 22 can irrigate endocardial tissue 110 with irrigation fluid 104, exiting from irrigation spray ports 72, in order to cool the endocardial tissue and reduce charring. As shown in FIG. 8, inner balloon 62 is inflated with inflation fluid 100 and outer balloon 64 is inflated with irrigation fluid 104.

As described supra, upon inflation module 76 inflating inner balloon 62 with inflation fluid 100 and irrigation module 76 inflating outer balloon 64 with irrigation fluid 104, splines 82 extend from longitudinal axis 86 in order to create channels 102 (i.e., longitudinal depressions) on the surface of the inner balloon in order to direct the irrigation fluid to irrigation spray ports 72. Channels 102 are typically aligned with electrodes 70 in order to optimize flow of irrigation fluid 104 to irrigation spray ports 72. Additionally, channels 102 prevent the inner and the outer balloons from touching each other, which can block the delivery of the irrigation fluid to one or more of the irrigation spray ports. Upon completing the ablation procedure, inflation module 78 can extract inflation fluid 100 from inner balloon 62 thereby deflating the inner balloon.

Figure 9:
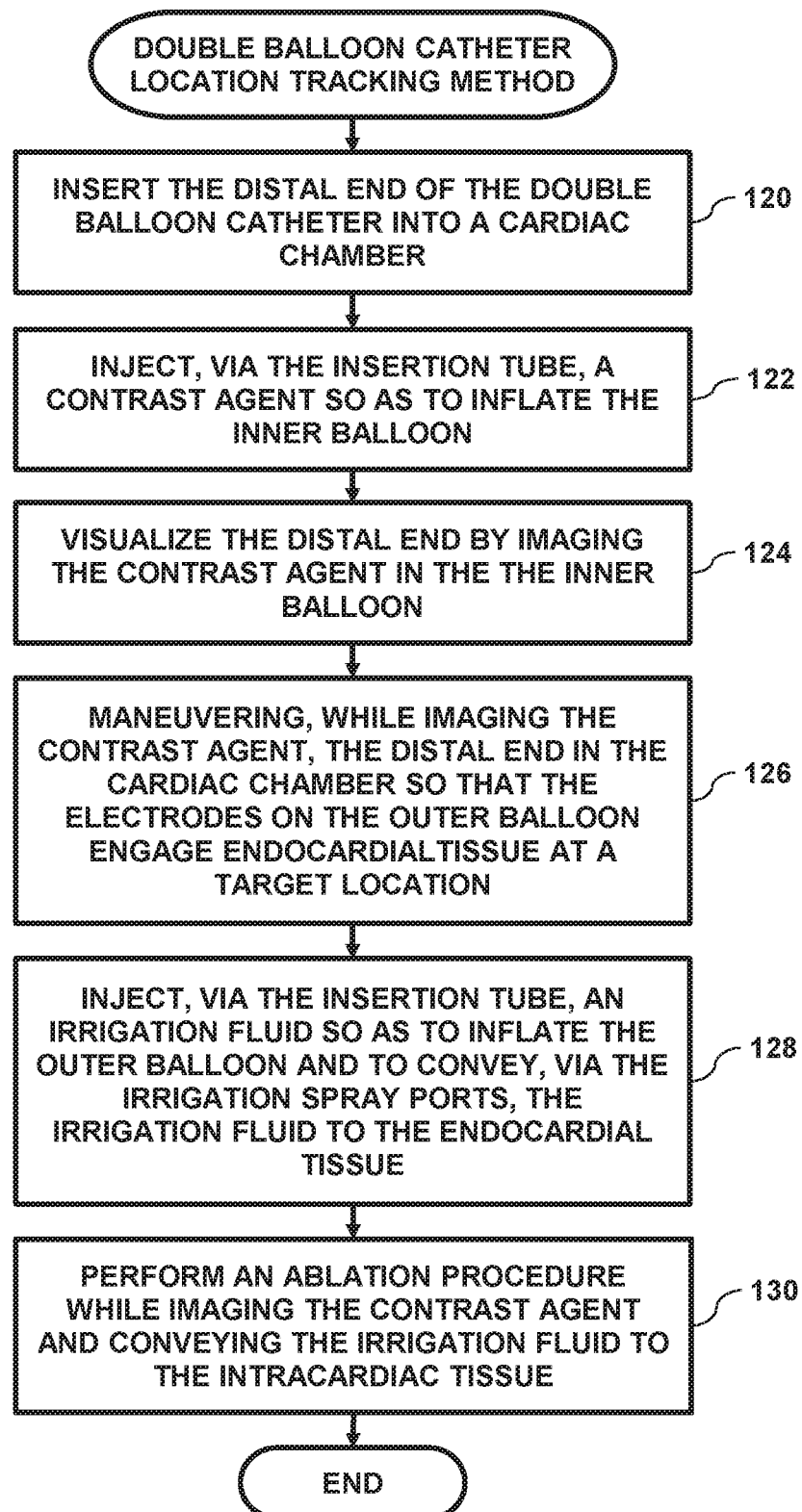
FIG. 9 is a flow diagram that illustrates a method of tracking the distal end during the ablation procedure, in insertion with an embodiment of the present invention.

FIG. 9 is a flow diagram that illustrates a method of tracking terminal member 36 during an ablation procedure, in insertion with an embodiment of the present invention. In a first positioning step 120, operator 32 manipulates insertion tube 30 so that distal end 26 of medical probe 22 enters a chamber of heart 28, and in a first injection step 122, inflation module 78 injects inflation conduit 68 with inflation fluid 100 thereby inflating inner balloon 62.

As described supra, inflation fluid may comprise a contrast agent that provides radiopacity for fluoroscopy unit 38. In response to fluoroscopy unit 38 imaging the contrast agent in inner balloon 62 and conveying the image information to console 24, processor 48 presents, in a visualization step 124, image 50 comprising a visualization of distal end 26.

While tracking distal end 26 during a maneuvering step 126, operator 32 manipulates insertion tube 30 to maneuver distal end 26 so that electrodes 70 engage a target location on endocardial tissue 110, and in an injection step 128, irrigation module 76 injects irrigation fluid 104 into insertion tube 30 in order to inflate outer balloon 64 and to convey, via channels 102 and irrigation spray ports 72, the irrigation fluid to the endocardial tissue. Finally, in an ablation step 130, using radio-frequency (RF) energy conveyed from ablation module 74, electrodes 72 perform an ablation procedure on endocardial tissue 110 while fluoroscopy unit images the contrast agent (i.e., inflation fluid 100) in the inner balloon and while irrigation spray ports 72 convey irrigation fluid 104 to the endocardial tissue. In embodiments of the present invention, steps 122, 128 and 130 are typically performed in response to inputs from operator 32 (e.g., via input devices 60).

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A medical apparatus, comprising:
   a flexible insertion tube having a distal end;
   a first conduit disposed in the flexible insertion tube;
   a second conduit disposed in the flexible insertion tube; and
   a terminal member fixed to the distal end and comprising:
      a first balloon comprising one or more spray ports, the first balloon being coupled to the first conduit;
      a second balloon contained within the first balloon, the second balloon being coupled to the second conduit; and
      multiple splines embedded in the second balloon, the splines comprising a flexible, resilient material and extending along a longitudinal axis of the terminal member, and configured to constrain the second balloon such that an expansion of the second balloon creates lobes and channels between the lobes.

2. The medical apparatus according to claim 1, and comprising one or more electrodes mounted on the first balloon.

3. The medical apparatus according to claim 1, and comprising a telescoping shaft contained within the second balloon.

4. The medical apparatus according to claim 3, and comprising a flexible sleeve surrounding the telescoping shaft.

5. The medical apparatus according to claim 1, in which the multiple splines have cross-sections selected from a group consisting of rectangular and elliptical cross-sections.

6. The medical apparatus according to claim 1, in which the flexible, resilient material comprises a shape-memory alloy.

7. The medical apparatus according to claim 6, in which the multiple splines have an original state.

8. The medical apparatus according to claim 7, in which the multiple splines are straight in the original state.

9. A method, comprising:
   inserting a distal end of flexible insertion tube into a body cavity, the flexible insertion tube containing first and second conduits configured to deliver first and second fluids, respectively, to a terminal member fixed to the distal end of the insertion tube, the terminal member comprising:
      a first balloon comprising one or more spray ports and coupled to the first conduit,
      a second balloon contained within the first balloon and coupled to the second conduit, and
      multiple splines embedded in the second balloon, the splines comprising a flexible, resilient material and extending along a longitudinal axis of the terminal member and configured to constrain the second balloon;
   conveying the first fluid through the first conduit, into the first balloon, and out through the spray ports;
   conveying the second fluid through the second conduit and into the second balloon; and
   creating, on the second balloon, lobes and channels between the lobes, that form, along the longitudinal axis between the lobes.

10. The method according to claim 9, in which the step of conveying the first fluid includes conveying the first fluid through the channels to direct the first fluid from the first conduit to the one or more spray ports.

11. The method according to claim 9, in which the first fluid comprises an irrigation fluid, and in which the second fluid comprises a contrast agent.

12. The method according to claim 9, in which the step of conveying the second fluid includes retracting a telescoping shaft disposed in the second balloon.

13. The method according to claim 9, in which the splines have cross-sections selected from a group consisting of rectangular and elliptical cross-sections.

* * * * *